United States Patent
Gautsch et al.

(10) Patent No.: US 6,706,498 B2
(45) Date of Patent: Mar. 16, 2004

(54) METHOD FOR ISOLATING DNA

(75) Inventors: James W. Gautsch, Solana Beach, CA (US); Michael G. Saghbini, San Diego, CA (US); David A. Lippman, San Marcos, CA (US); Richard C. Dana, Escondido, CA (US)

(73) Assignee: Bio101, Inc., Vista, CA (US)

( * ) Notice: Subject to any disclaimer, the term of this patent is extended or adjusted under 35 U.S.C. 154(b) by 0 days.

(21) Appl. No.: 09/863,137

(22) Filed: May 22, 2001

(65) Prior Publication Data
US 2002/0172949 A1 Nov. 21, 2002

Related U.S. Application Data

(63) Continuation of application No. 08/937,905, filed on Sep. 25, 1997, now Pat. No. 6,235,501, which is a continuation of application No. 08/388,504, filed on Feb. 14, 1995, now abandoned.

(51) Int. Cl.[7] .......................... C07H 1/00; C07H 21/00
(52) U.S. Cl. ................ 435/91.1; 435/259; 435/270; 435/173.7; 435/91.3; 536/23.1; 536/25.4; 536/25.41; 241/2
(58) Field of Search ............................... 435/91.1, 259, 435/270, 173.7, 91.3; 536/23.1, 25.4, 25.41; 241/2

(56) References Cited

U.S. PATENT DOCUMENTS

| | | | | |
|---|---|---|---|---|
| 5,464,773 A | * | 11/1995 | Melendez et al. | 435/306.1 |
| 5,567,050 A | * | 10/1996 | Zlobinsky et al. | 366/209 |
| 6,235,501 B1 | * | 5/2001 | Gautsch et al. | 435/91.1 |

FOREIGN PATENT DOCUMENTS

| EP | 0 288 618 | * | 2/1988 |
|---|---|---|---|

OTHER PUBLICATIONS

1995–1996 Cole Parmer Catalogue, pp. 538, 539, 547, 548, 1994.*
1988 Fisher Catalogue, p. 609, 1988.*

* cited by examiner

*Primary Examiner*—Pranoisco Prats
(74) *Attorney, Agent, or Firm*—Gray Cary Ware & Freidenrich, LLP; Lisa A. Haile; Michael Rosato

(57) ABSTRACT

The invention describes a method for the isolation of components from samples, particularly large molecular weight DNA from biological samples. The method involves the application of controlled oscillatory mechanical energy to the sample for short periods of time of about 5 to 60 seconds to lyse the sample and release the component(s) from the sample, followed by standard isolation methods. In preferred embodiments, the method includes the use of a spherical particle for applying the mechanical energy.

20 Claims, 11 Drawing Sheets

METHOD FOR ISOLATING DNA

FIELD OF THE INVENTION

This invention relates to reagents, methods and apparatus for the isolation of cellular components such as deoxyribonucleic acid (DNA), ribonucleic acid (RNA), proteins and other materials from natural cellular sources or other sources containing these materials.

BACKGROUND OF THE INVENTION

Cells contain a wide variety of cellular components appropriate to their function. They contain, for example, DNA and their expression products including a host of proteinaceous materials. This invention is useful for the isolation of such cellular components, but in particular, the invention is principally suited for the isolation of nucleic acids, DNA and RNA.

DNA is a critical component in the sequence of biological reactions which results in the expression of the myriads of proteins including hormones, enzymes and structural tissue essential for the existence of all forms of life. There is a critical need for small and large amounts of DNA for research purposes as well as diagnostic and therapeutic uses.

Plant/animal cells, tissues and organs, insects and microorganisms including viruses, yeast, fungi, algae and bacteria, and other materials are potential sources of DNA. However, the structural organization of some of these sources can be so strong such that it is difficult, time consuming and may require expensive equipment to isolate DNA from those tissues.

For instance, DNA isolation from certain bacteria is difficult because the cell walls are not readily susceptible to lysis. Current protocols for isolating DNA from bacteria frequently employ enzymes such as lysostaphin or lysozyme to digest the bacterial cell wall followed by the addition of denaturing agents to lyse cells and inactivate the nucleases.

BRIEF SUMMARY OF THE INVENTION

The isolation of nucleic acids from various sources, particularly plants, yeast, bacteria, and certain tissues, such as muscle, bone, cartilage, seeds, bark and the like, is difficult due to the presence of cellular structures which protect the tissue, such as rigid cell walls, or other rigid structures, and therefore difficult to rupture completely with commonly used buffers. Removal of these obstacles is tedious and not always feasible with available methods. Variations in nucleic acid yield and quality from the various extraction procedures probably arises from the non-homogeneity (inconsistency) of the tissue as it is broken up. Thus, there is a need for a new technique for disrupting the tissue by a thorough, yet delimited mechanism to allow the rapid isolation of nucleic acids in a reproducible manner without the need to excessively homogenize the cells or tissues.

Procedures have now been discovered which makes possible the separation and isolation of large molecular weight DNA of exceptionally high quality in high yields from a variety of tissues. These procedure are very convenient and can be completed in a very short period of time, typically less than one half hour. This process is, moreover, applicable not only to intact biological tissue but also to microorganisms such as bacteria and yeast, and also to plant tissues as sources of DNA. Such sources, especially bacteria, yeast and plants are much more convenient than complex biological tissue from higher organisms as a source of DNA because they are uniform, readily available in any desired quantities and easier to work with than biological tissue.

The novel procedure of this invention comprises the application of sufficient mechanical energy to the cell walls of the selected DNA source to disrupt the cell walls and release the DNA. The essence of this invention is the discovery of the present methods for tissue or cell disruption in which the tissues and/or cell walls are fractured by specified forces created by the reciprocal motion producing the mechanical energy in a container with the tissue and liquid medium, thereby releasing the DNA from the tissue and into the medium.

In some preferred embodiments, the method includes the use of tissue and/or cell wall fracturing particles in the disruptive media in a closed container.

After lysis of the tissue, the released DNA can be recovered in high yield and purity by any of a variety of recovery methods. Exemplary DNA recovery methods are described further herein.

There are a number of advantages provided by the process of this invention especially when conducted for the isolation of DNA. These include:

1. Applicability to DNA sources such as bacterial cells, fungi, plant cells and other intractable sources which have heretofore been refractory to homogenization procedures with any other extractant media or manipulation.
2. Recovery of DNA as a high yield product substantially uncontaminated by other cellular components.
3. Applicability to the production of both small and large quantities of DNA in batch, multiple sample or continuous processes.
4. Completion in a very short period of time.
5. No ultracentrifugation is required.
6. Isolation of high molecular weight DNA.
7. The reagents used in the methods of the invention are substantially non-toxic, odor free and readily available at commercially attractive prices.

DETAILED DESCRIPTION OF THE INVENTION

Figure 1:
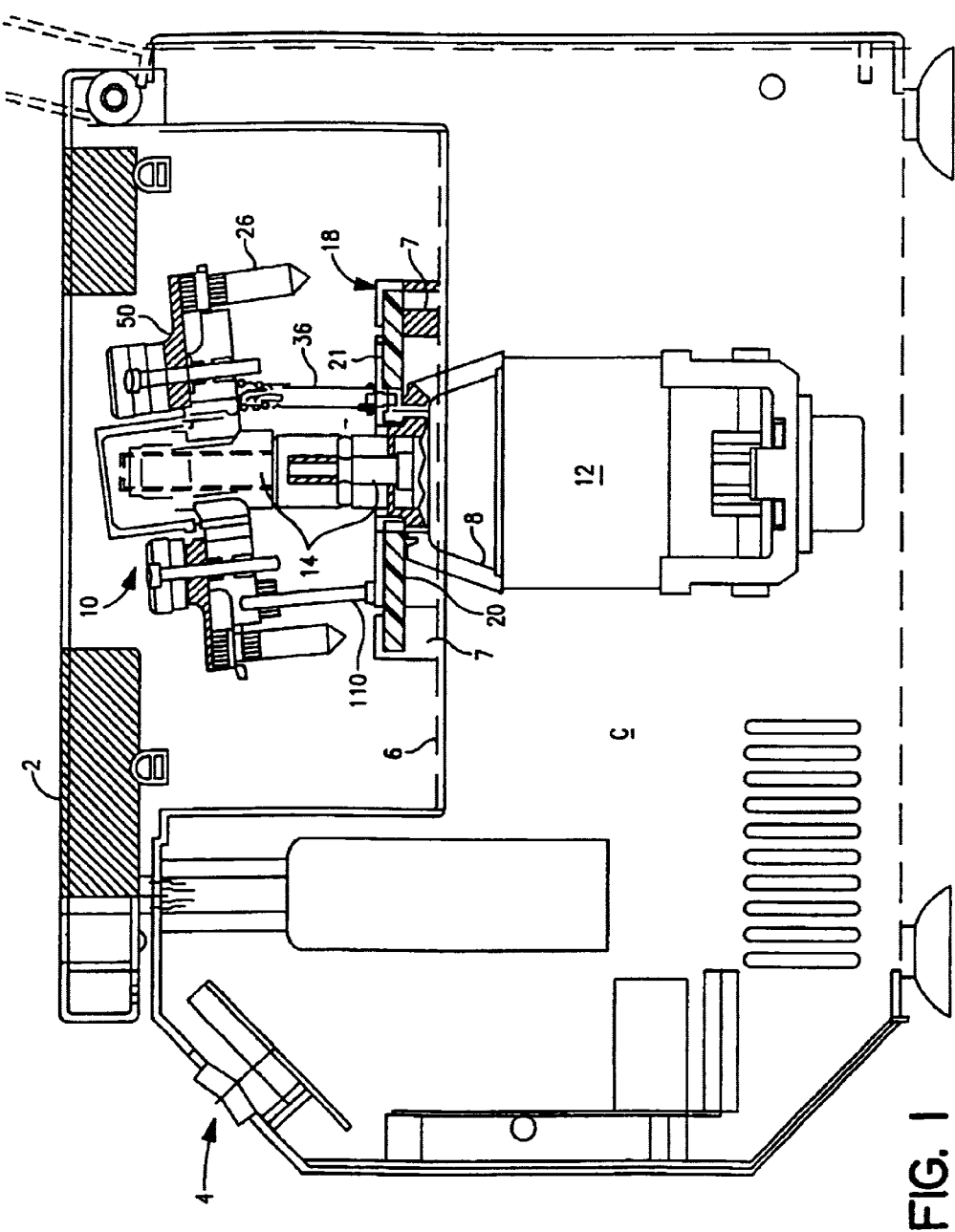
FIG. 1 is a vertical side elevational view of the apparatus used in the invention as it is housed in a casing, a side wall of the casing being removed for convenience of depiction and some parts being shown in section, there being depicted several specimen containing vessel receivers on the holder disc and showing further a tilting of the vessel holder in a position denoting the vertical extremes of the vertical oscillating movement to which it is subjected during apparatus operation.

The present invention provides for the separation of components in a sample, and particularly for the isolation of nucleic acids such as DNA from a tissue. The method is based, primarily, on the discovery of procedures for disruption of a sample, tissue or cell by the application of large controlled mechanical energy to the sample in a short period of time, thereby facilitating the separation of components in the disrupted sample.

In a preferred embodiment, the invention describes a method for the isolation of high molecular weight DNA from a tissue or other sample. However, although many of the descriptions recite DNA isolation as exemplary for the methods, these descriptions are made for convenience and to avoid redundancies. Therefore, the method is not to be construed as limited to DNA isolation but rather to be read on the isolation of any sample component where disruption facilitates isolation according to the present methods.

The first step in the practice of this invention is to mechanically fracture the cell walls, subcellular organelles, and/or tissue or extra-tissue structure of the DNA source material by the application of the controlled mechanical energy in a liquid medium containing the DNA source material. The DNA source material can be bacteria, eukaryotic cells of a biological tissue, plant, yeast or fungi cells, or non-cellular material, such as processed or unprocessed food, gels, soil sample, industrial solutions, and the like materials.

The application of uncontrolled mechanical energy leads to efficient tissue homogenization, however, the isolated DNA is typically of relatively small size which is undesirable for a variety of uses. The present methods for applying mechanical energy produce DNA of large molecular weight, typically greater that 10 kilobases (kb) average molecular weight.

Following fracture of the DNA source material, thereby releasing the DNA from its structural confines in the source material, the DNA is recovered. Recovery of DNA can be conducted by any of a variety of methods, although certain recovery procedures are preferred.

A. Mechanical Lysis of the Tissue Source

An important aspect of the mechanical energy involved in sample, tissue or cell disruption in accordance with this invention is that the energy is reciprocally applied in an oscillatory motion to a liquid medium containing the sample, thereby exerting a force sufficient to disrupt the tissue structure sufficient to release the DNA from the sample material's organized structure, such as cellular organelles of a tissue, into the liquid medium.

In some preferred embodiments, the mechanical energy is exerted in the presence of one or more particles which function to impact the tissue, mix the liquid medium, and otherwise assist the isolation process.

The applied mechanical energy is controlled by the presence/absence of particles of different sizes, shapes and densities, together with the choice of oscillation conditions (speed, periodicity, acceleration, etc.). Different materials as DNA source require application of different mechanical energies for efficient homogenization of the material and release of large molecular weight DNA. Examples of different applied energy conditions for different materials are given later.

Rotational energy such as generated with a blender or other homogenizer is not useful because the fragments of tissue, or cells of the tissue, simply rotate and do not collide with each other or the components of the liquid medium under sufficient mechanical energy of an oscillatory nature to lyse the tissue components and release nucleic acids.

1. Apparatus for Applying Mechanical Energy

It is known in the art to mechanically lyse source material to release genetic material such as RNA or DNA. Generally this involves subjecting the source material to mechanical force and energy that disrupts the cells with violent impact action with consequent release of the nucleic acids. The released DNA or RNA then is recovered, e.g., from a liquid phase of the starting material, such procedure being known in the art.

One mechanical lysing protocol previously described for isolating DNA employs bead mill separation, this source material being confined in a vessel in a liquid phase thereof, there also being minute or small sized beads contained in the vessel. Rapid oscillation of the vessel is used to impart impact energy to the beads and these strike the source material cells repeatedly to open the cells so the nucleic acids can be released.

Certain known separation devices and particularly bead mill types are limited as to production capacity, i.e., the number of specimen vessels that can be oscillated at one time. For example BEAD BEATER bead mills manufactured by BioSpec Products of Bartlesville, Okla., for a long time only could be used to oscillate one specimen at a time, although recently a bead mill for use with up to eight specimen vessels at one time has been introduced. These bead mills either single or plural specimen holding, operate to reciprocate the specimen holding vessels horizontally with respect to a horizontal axis defined by a rapidly rotating shaft that drives the oscillating mechanism. Where plural specimen vessels are oscillated together, they have been clustered close about the horizontal axis. A disadvantage of that arrangement is that reproducibility of oscillating conditions to be the same in each vessel is difficult, if at all possible, to achieve. Where a separation protocol is to be practiced, conditions occurring in each specimen should be replicated identically in each.

Oscillating a cluster of specimen vessels along a horizontal or near horizontal axis and involving use of bead mills of the above description presents serious balance problems in the oscillation producing mechanism creating destructive effects leading to abort mechanism service life, the effect of horizontal oscillation on the mechanism bearing unit, for example, being most extreme.

Another shortcoming of known bead mills is lack of capacity to produce oscillations greater than about 2800 oscillations per minute (about 46 Hz). As a result, these bead mills are not capable of efficiently disrupting tissues, particularly tissues having a medium or hard structure and cells of certain types, and hence resort must be had to chemical lysing.

In dealing with the quest for improving mechanical lysing of tissues for release of cellular components, particularly nucleic acids, it is seen that an apparatus that allows simultaneous separation of plural samples at very high oscillating rate while maintaining optimum balance in the apparatus is required, this being attributable in part to understanding that to combine high oscillation rate with high average linear acceleration in the material is difficult, but necessary to practice the present invention.

The present apparatus more rapidly effects mechanical separation of nucleic acids, and particularly DNA, from a source thereof and does so without adverse effect on the nucleic acid. The apparatus operates at speeds as high as 166 hertz (Hz), i.e., about 10,000 oscillations per minute and is effective to impart average linear acceleration to a source material of up to about 450 times gravity (×g) or more thereby producing relatively complete lysis and release of nucleic acids in a time period that can be as low as from about 3 seconds to about 5 minutes where a specimen vessel of typically 100 microliters (ul) to about 5 milliliters (ml) volume is used to contain the specimen (50–2,000 ul) and about 200 ul to 3 ml of liquid.

Briefly stated, there is provided by use of the apparatus described herein a method for rapidly oscillating specimen containing vessels in a nucleic acid recovery operation wherein controlled mechanical force is employed to disrupt the cell walls and tissue structure of a tissue used as a source of the nucleic acids. The disruption, or lysing, of the tissue by mechanical means involves accelerating the source material to relatively high g (acceleration imparted to a body by gravity acting in a vacuum being one g) levels in an oscillatory fashion in a short time to expose it to an average linear acceleration that will produce sufficient mechanical energy in the source material that produces the cell disruption or fracture to allow release of nucleic acids from the organized structures of the cells of the tissue.

The apparatus includes a specimen vessel holder provided as a disc in which the vessels are received. The disc is operably connected with oscillatory motion producing means that in operation oscillates the disc rapidly in an oscillatory movement up and down symmetrically on a fixed vertical axis. The disc is haltered so it cannot rotate about the fixed axis. Locking means in the form of a locking plate locks the vessels on the vessel holder and applies clamping force thereto to prevent relative movement between the vessels and the holder so that generation of heat that could be detrimental to the specimen material or the vessels holding same is obviated.

The apparatus for rapidly reciprocally vibrating specimen-containing vessels accelerates a specimen material (tissue) in the vessels to relatively high g levels. In one embodiment, the apparatus includes a disc shaped vessel holder, the vessel holder having vessel receptive structure arrayed thereon at a plurality of circularly spaced locations proximal a disc edge periphery for receiving and holding up to a corresponding plurality of specimen vessels thereon. A vertically oriented rotary shaft rotatable about a fixed axis has a mounting collar fixed thereon to rotate therewith. The mounting collar has an outer surface, this outer surface being symmetrical about an axis skewed longitudinally of the fixed axis. The vessel holder is mounted on the collar outer surface such that the vessel holder vessel receptive structure is symmetrically arrayed with respect to the skewed axis and such that there is relative rotatability between the mounting surface and the vessel holder. When the mounting collar is rotated by rotary shaft rotation and the vessel holder not held, it tends to rotate in unison with the mounting collar about the skewed axis but if the vessel holder is held against this tendency to rotate with the mounting collar, the vessel holder will be caused to oscillate vertically up and down symmetrically of the fixed axis with any given point at the disc edge periphery undergoing one complete oscillation for each rotary shaft about said fixed axis, as is means for haltering the vessel holder so that it cannot rotate in unison with the mounting collar.

In another embodiment, the apparatus comprises a disc shaped vessel holder, along with a vertically oriented rotary shaft rotatable about a fixed axis with the vessel holder being mounted on the rotary shaft such that there can be relative rotatability therebetween. Means are provided for holding the vessel holder to constrain a rotation of the vessel holder if the rotary shaft is rotated. Oscillatory motion producing means is operably connected with the rotary shaft and the vessel holder and is operable such as to cause the vessel holder to oscillate vertically up and down symmetrically with respect to the fixed axis when the rotary shaft is rotated, any given point at an edge periphery of the disc undergoing one complete oscillation for each rotary shaft revolution. The disc shaped vessel has a circularly arrayed uniformly spaced plurality of specimen vessel receptive openings therein located proximal the edge periphery of the vessel holder, with a center of each opening being equidistant from the fixed axis whereby an oscillation produced acceleration to which a material contained in a specimen vessel received in an opening is subjected, is substantially the same with respect to that produced in a specimen vessel received in another opening.

The apparatus can subject the specimen material to oscillations at an oscillatory rate of between about 25 Hz to about 133 Hz and can produce an average linear acceleration in the source material which is in a range of about 150×g to about 415×g for a period of between about 3 seconds to about 5 minutes.

The apparatus uses a vessel or container useful for containing a specimen material which is to be subjected to a specimen treatment during which treatment, the vessel and or specimen material can be exposed to heat that could be detrimental to specimen and/or vessel integrity, this vessel being a sealable member having an inner specimen compartment for holding a specimen material, and an outer casing surrounding the inner compartment in which a freezable or readily cooled fluid can be received so that when such fluid has been frozen or cooled to very low temperature and the contained specimen subjected to said treatment, the specimen in the inner compartment and the vessel structure is temperature protected from heat produced incident the treatment by preferential transfer of heat into the fluid. Means such as removable caps for sealing an entry to each of the inner compartment and the outer casing are provided.

Using the apparatus described herein, average linear accelerations can range between from 150 g up to at least about 415 g or more. Further, oscillation rates of up to at least about 116 Hz to 133 Hz or more are possible. A Hz is a unit of frequency, and 1 Hz is equal to one cycle per second. For example, 116 Hz corresponds to an oscillation rate of 7000 and 133 Hz to a rate of 8000 cycles per minute.

In practicing a protocol it is convenient to use inexpensive, disposable plastic vessels or vials for holding the source material.

The apparatus is intended particularly for use in a laboratory environment wherein it will be seated on a counter or table top readily accessible for use by the scientist or technician. For that reason it will be housed in a casing having a cover, and since the apparatus is portable and of reasonable weight and size is readily movable from one to another laboratory location without difficulty. The casing preferably will be fitted with suction cups at the underside as these obviate any movement action of the casing along a counter top during operation, and caused by operation vibrations. To further diminish vibration effect, the apparatus is isolated from the casing by vibration absorbing means.

FIG. 1 depicts a casing C in which the apparatus 10 is housed. The casing C includes a cover 2 which is closed during the apparatus operation, and it can be provided with safety interlock features such that the cover is locked and cannot be opened during operation and that the drive motor operating the apparatus cannot be activated unless the door is closed. Such features are considered essential to protect personnel and prevent injury from apparatus that operates at extremely high speeds.

Within the casing, a fixed support drum 6 will mount the apparatus through the intermediate vibration absorbing anchor structure to be described later. In this manner no serious or undesirable vibration effect will transmit from the operating apparatus to the casing structure. The casing C also will mount controls such as switches, timer unit etc., these being shown generally at 4. Further, the casing can include a fan unit therein to circulate a stream of cooling air against the apparatus to carry off heat therefrom which is generated during operation and particularly in the bearing unit that will be described later.

Figure 2:
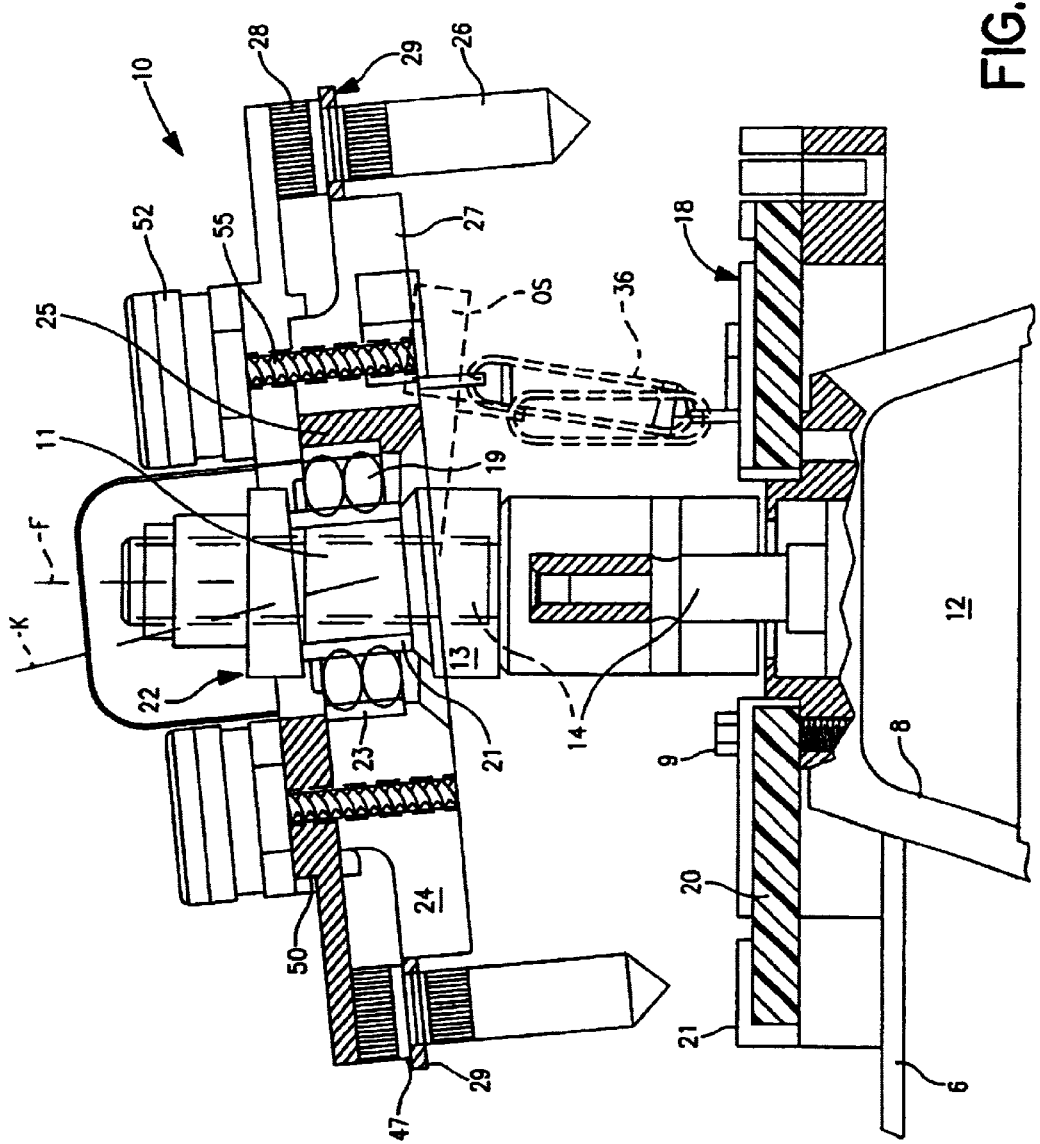
FIG. 2 is a fragmentary view of the FIG. 1 apparatus on enlarged scale.

With reference to FIG. 2, the apparatus 10 comprises a drive motor 12 having a vertically oriented output or drive shaft 14 which is rotatable about a fixed vertical axis, the motor being hung or suspended from anchor structure shown generally at 18, the motor being capable of rotating at speeds up to at least about 8000 R.P.M. The anchor structure 18 includes a plate 21 and blocks 7 on which it is set, the blocks in turn being mounted on drum 6. Intervening the plate 21 and the blocks 7 is a resilient material pad 20 which preferably is of rubber and one which exhibits stiffness in respect of a twisting thereof yet is readily flexible and yielding in respect of vertical force applied thereto. Pad 20 serves to damp vibrations transmitted through the plate 21 that otherwise could enter the drum 6 and transmit to the casing C.

The upper part of the housing 8 of the motor 12 is connected to the plate 21 as by bolts 9 (only one shown) and in such manner the motor and the remainder of the apparatus is suspended mounted thereby lessening vibration generation in the apparatus and casing.

The single suspended mounting of the apparatus is particularly effective to the purpose of minimizing operation produced vibrations, this being achieved with use of a single relatively thin disc shaped pad member 20 and placement of the orientation of the pad member to be planar perpendicular to the fixed axis F. The pad member as noted above is selected as a rubber component exhibiting two stiffness. With respect to torque force circularly acting in direction perpendicular to axis F, the pad is extremely stiff which is desirable from the standpoint of dealing with torque as a factor in vibration cause. On the other hand and with regard to force acting parallel to the axis F, the pad material is very soft, i.e., has little stiffness so that the force is readily damped by the flexibility of the pad in that force direction.

The apparatus includes oscillatory motion producing means shown generally at 22, the oscillatory motion producing means being of a type similar to that used to produce a like motion in the earlier-mentioned BioSpec bead mills. Such means includes an eccentric mounting collar 11 integral with a hub 13, this unit being screwed on to shaft 14 and rotatable with shaft 14.

This oscillatory motion producing means also includes a bearing unit comprised of an inner race 21 clamped between hub 13 and a nut 15 threaded on shaft 14 so as to be fixed to rotate with the mounting collar, an outer race 23 fixed to a central bore of a relatively widened, relatively shallow vessel holder 24 made preferably in the shape of a disc located a distance above the anchor structure, and a plurality of ball bearings 19 captive between the races. A preferred form of bearing is a double row angular contour ball bearing.

The mounting collar 11 has an outer surface which is symmetrical about an axis K which is skewed longitudinally of the fixed shaft axis F. Thus it is seen that the vessel holder 24 is mounted on the mounting collar such that vessel holder vessel receptive structure (to be described shortly) is symmetrically arrayed with respect to this skewed axis K. Further it is seen that relative rotatability exists between the vessel holder and the mounting collar.

With this arrangement, it is seen that if the vessel holder 24 not be held during rotation of the mounting collar 11, the vessel holder would be caused to have a certain rotation in unison with the mounting collar about axis K, such rotation being at the inclined solid line showing of the vessel holder in FIG. 2. On the other hand, if the vessel holder 24 is haltered or held during mounting collar 11 rotation, the vessel holder will be caused to oscillate vertically up and down and symmetrically with respect of fixed axis F. This movement is illustrated in exemplary showing in dashed line vessel holder fragment positioning as at OS in FIG. 2.

It will be understood that this vertical oscillatory movement of the vessel holder occurs such that any given point at the periphery of the vessel holder will undergo one complete oscillation up and down each time shaft 14 and mounting collar 11 make one complete revolution.

Vessel holder 24 in a preferred form is a disc having a hub 25, a number of arms 27 emanating from the hub and terminating in an annular periphery ring 29. Annular periphery ring 29 it will noted is of much lesser thickness than the thickness of radially inwardly parts of the vessel holder, this being desirable to reduce the mass of the holder.

Since considerable heat will be generated in the apparatus and particularly in the bearing unit during operation, it is desirable that the disc mass function as a heat sink to carry off heat, the disc for that reason being of a material which has good heat conductivity characteristic, aluminum being exemplary of such material.

The vessel holder 24 will have suitable structure thereon for reception and holding of a plurality (e.g., at least 18) of specimen containing vessels, the depicted ones of such being scalable vials 26, the vials being fitted with seal caps 28.

In simplest form, this holding structure can be constituted of a circle of uniformly spaced openings 32 carried in annular periphery ring 29 and passing therethrough from one to an opposite face. In this manner a vial body passes down through an opening 32 until its vial flange 47 engages the upper disc face adjacent the opening to hold the vial mounted on the disc. Other forms of holding structure or devices could be used instead of openings.

In connection with openings 32, a center of each is equidistant located from a center of the holder. In this manner, a specimen contained in a vessel received in an opening will be subjected to the exact same average linear acceleration values to which a specimen contained in a vessel received in any other opening 32 is subjected ruing apparatus opening. It is to be noted that average linear acceleration imparted to the specimen will be the same if only one vial is mounted on the vessel holder as that attendant mounting of a full complement of 18 vials on the vessel holder.

This sameness of replication of achieved linear acceleration for each separation protocol of each specimen whether for one or for 18 specimens at the same time, and stemming from symmetrical positioning of vessels on the vessel holder is seen as a major improvement over prior separating apparatus.

A halter means is used to prevent rotation of the disc 24 in unison with the mounting collar 11 during apparatus operation. This halter means can be, e.g., a tension type coil spring 3 connected to the disc at any underface part thereof and with the anchor structure 18, connection to the anchor structure minimizing extraneous vibration transmission to the spring. The spring 36 will be connected to the underface of the disc 24 at a radial location thereon which is closely proximal the shaft 14 and such that the spring disposes parallel to fixed axis F, this being done to limit the degree of tensing produced in the spring thereby reducing fatigue effect and lengthening spring useful service life.

By haltering the disc 24, oscillatory motion producing means drive effect thereon is as mentioned above to rapidly vertically oscillate the disc, periphery of the disc ring describing an imaginary rolling wave course about the shaft 14, it being understood that there is no circular travel of the shaft during oscillation thereof.

The result is that the vials 26 are rapidly oscillated in vertical reciprocal movements at a rate of as much as eight thousand oscillations per minute (133 Hz). Due to that rapid oscillatory movement of the vial, average linear acceleration values of up to 415 g are produced in the vial contents and the small sized bead in the vial produce very high impact magnitudes as they collide with the cells of nucleic acid source material therein and produce significant cell disruption to allow nucleic acids to release from the cells.

Depending on the type of tissue source material involved, essentially full release can be effected very quickly and in a time period ranging from about 10 to about 120 seconds and particularly in a range, depending on the material, of from about 10 to 30 seconds to about 30 to 60 seconds.

Because of the nature of the oscillatory movement to which the vials 26 are subjected, it is necessary to securely lock the vials on the disc periphery ring 29 so that during oscillation, no relative movement occurs therebetween as such relative movement could create high friction and consequent heat problems in the specimen and in the vessel.

Figure 3:
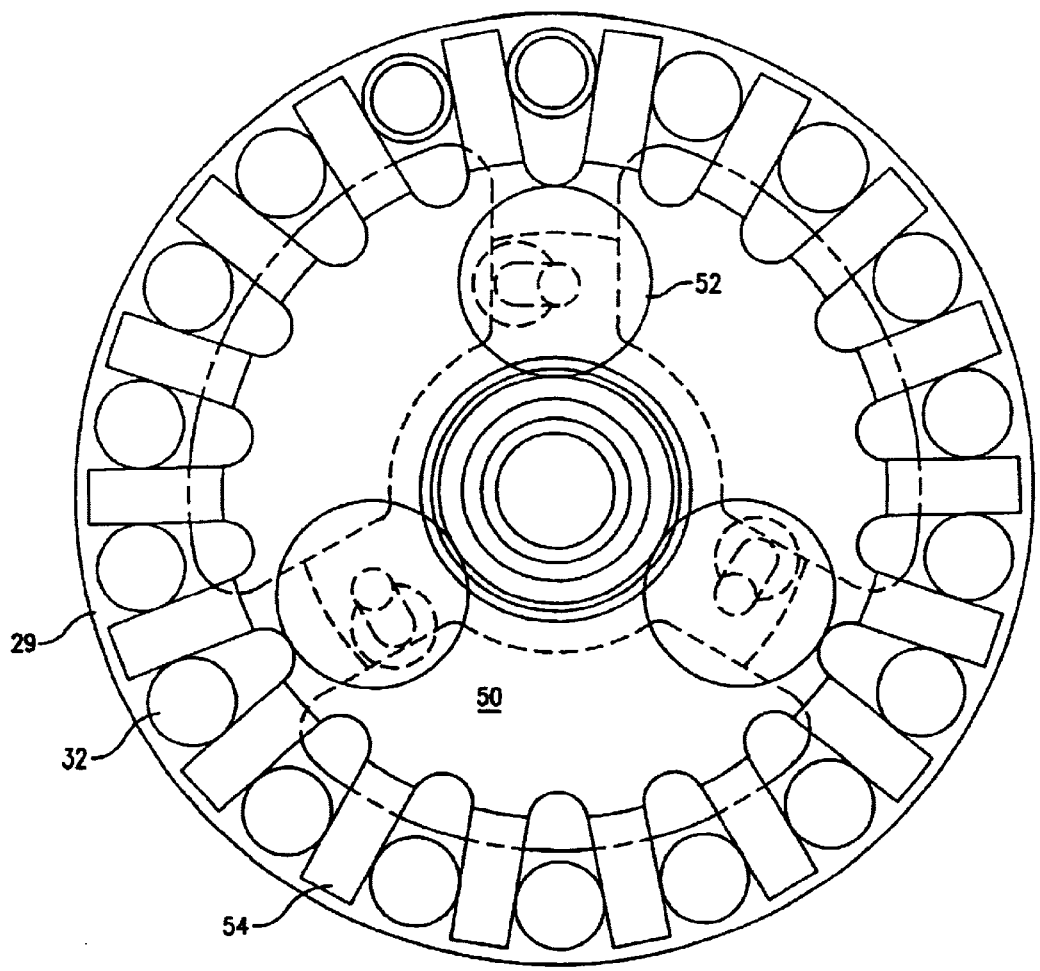
FIG. 3 is a top plan view of FIG. 2 and illustrates a fingered locking plate employed with the apparatus and having a lock member to lock the specimen vessels securely on the vessel holder to prevent relative movement between the vessels and the holder during oscillatory movement of the holder, the locking plate being in a clearing position as required for access to the holder receptor structure when mounting and demounting vessels.
Figure 4:
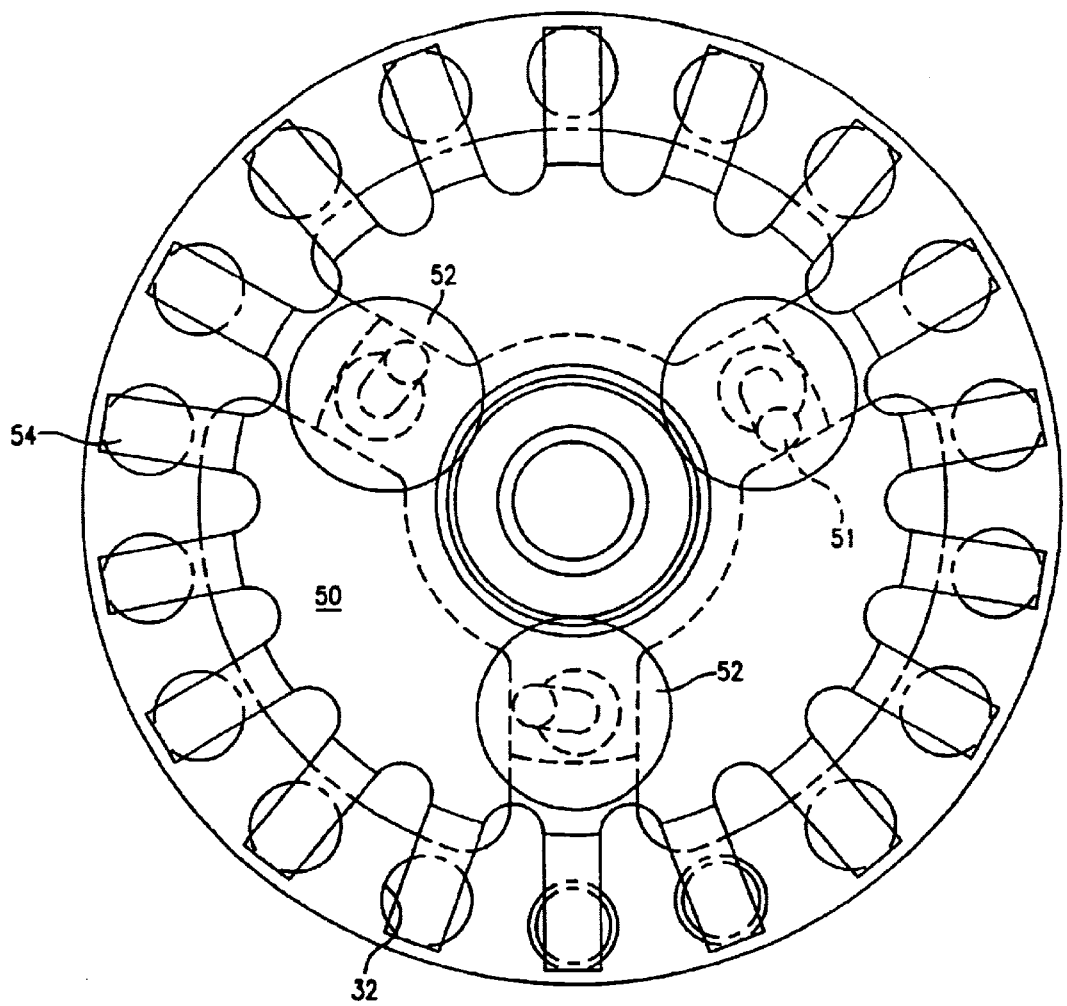
FIG. 4 is a view the same as FIG. 3 except the locking plate is shown in a circularly moved position wherein the fingers thereof superpose over the tops of the vessels and apply force to hold the vessels against movement relative to the holder during oscillatory movement.

To obviate such possibility, the locking of the vials is done with a locking plate 50 as shown in FIGS. 3 and 4. The locking plate 50 is mountable on top of the disc 24 and can be secured to the latter with a number of locking members or hand manipulated knobs 52 threaded as at 55 into passages in the disc, tightening of the knobs to friction holding degree locking the fixing plate against the disc.

As shown in respective clearing and covering dispositions in FIGS. 3 and 4, the locking plate 50 has blind slots 51 therein so it is circularly movable on the disc to accommodate loading/unloading of vials on the disc on the one hand, and securely clamping the vials in place on the disc on the other hand.

To securely hold the vials, the locking plate 50 has a circle of spaced radial fingers 54 in correspondence to the number of vial receptive openings in the disc. These fingers 54 when locking plate 50 is in locking position, engage the top of the vial caps 28 and apply hold down force to the vials. The urging is to forcefully hold the vial flange 47 against the upper face of the disc periphery ring 29 adjacent the openings 32 in the disc. This bars relative movement between the vials and the disc during operation.

Figure 5:
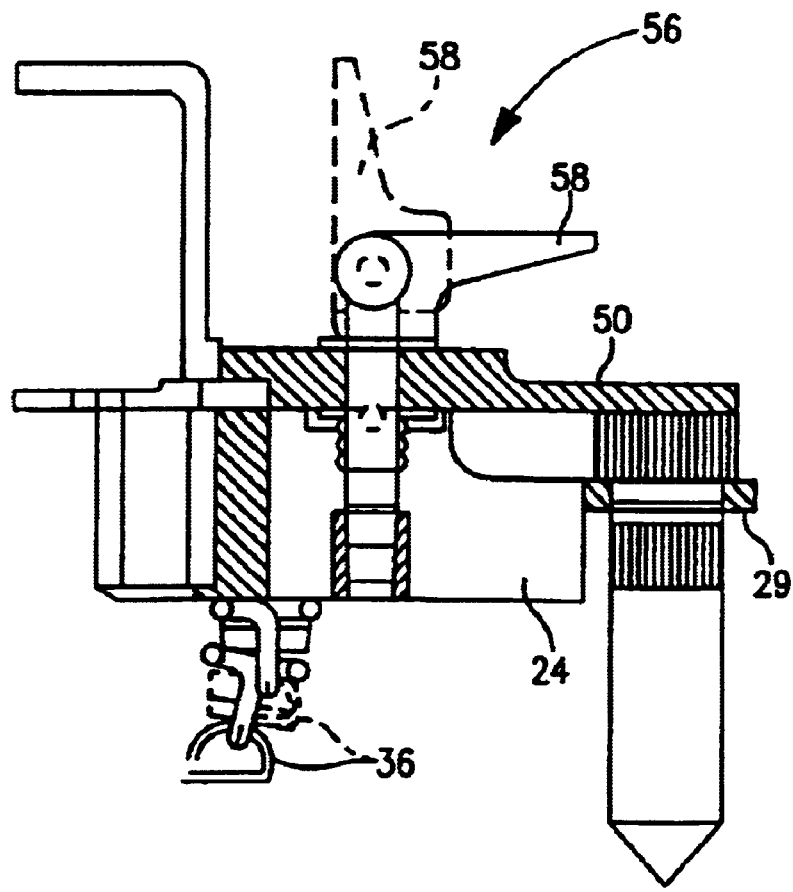
FIG. 5 is a fragmentary vertical sectional view of a peripheral portion of the vessel holder depicting another form of lock member for clamping the locking plate tightly against the holder so that clamping force is exerted by the fingers against vessel tops.

FIG. 5 shows another form of locking member 56 for clamping or locking the locking plate tightly against the vials and disc. It comprises a spring locking member unit which is depicted in unlocked position in dashed lines. By rotating the locking member arm 58 to the solid line position, a camming hold down effect is instituted.

Figure 6:
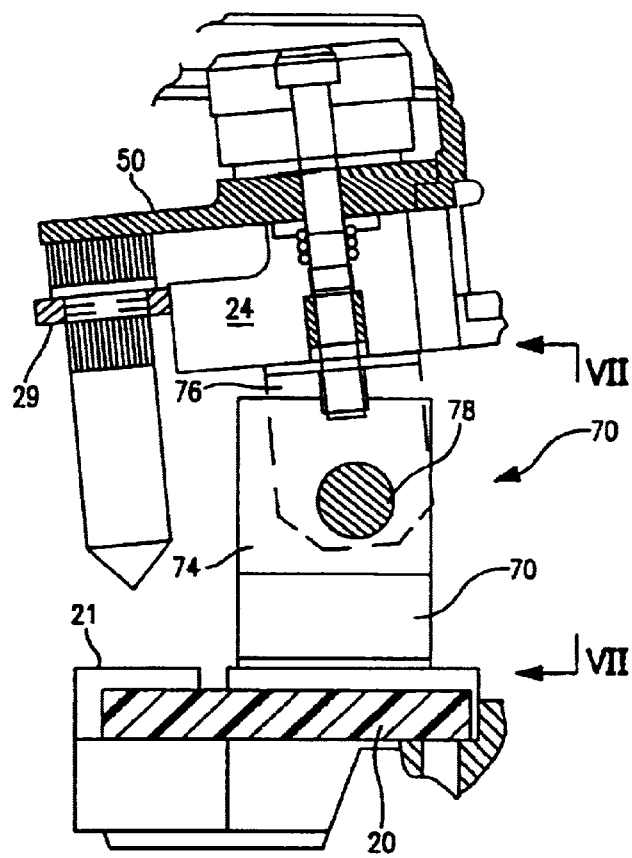
FIG. 6 is a fragmentary elevational view of a portion of the vessel holder and an anchor structure showing halter means wherein magnets are employed to halter the holder against rotation in unison with the mounting collar during operation of the apparatus.
Figure 7:
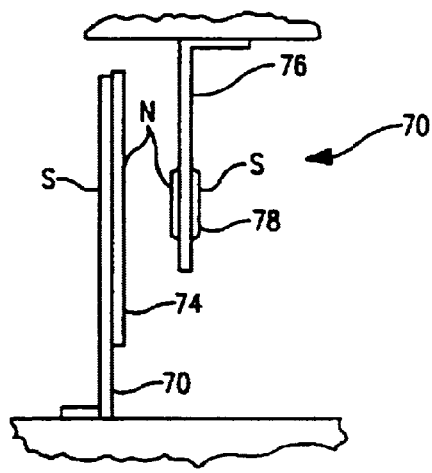
FIG. 7 is a fragmentary elevational view taken on the line VII–Vii in FIG. 6.

Other forms of haltering means can be used with the apparatus, these being advantageous if spring fatigue is a problem with the earlier described haltering means. FIGS. 6 and 7 depict a haltering means 70 provided with permanent magnets. In such means 70, a bracket 72 carried on the anchor frame mounts a permanent magnet 74, and a bracket 76 carried on the underside of the disc 24 mounts a permanent magnet 78. These permanent magnets are arranged in a confronting disposition, and the poles thereof arrange so that like poles face each other. This creates a magnetic repelling force that acts against the disc 24 so that if it tends to rotate in unison to any degree with the mounting collar during apparatus operation, the magnet repelling force prevents such disc rotation. It is to be understood that at least one of the magnet members will be of greater vertical dimension than the other to take into account the relative vertical movement of the magnet mounting elements that occurs during oscillation.

Figure 8:
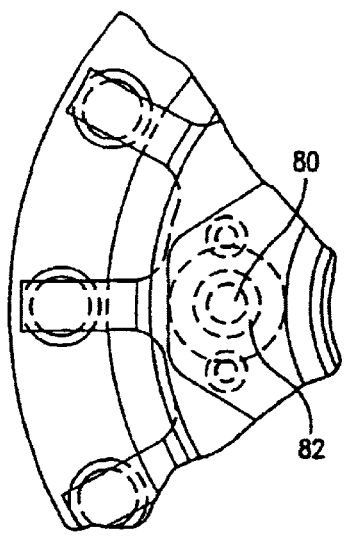
FIG. 8 is a fragmentary plan view of a peripheral portion of the vessel holder illustrating a further embodiment of halter means wherein a post and keeper ring are used, one of such elements being mounted on the anchor structure and the other on the vessel holder.
Figure 9:
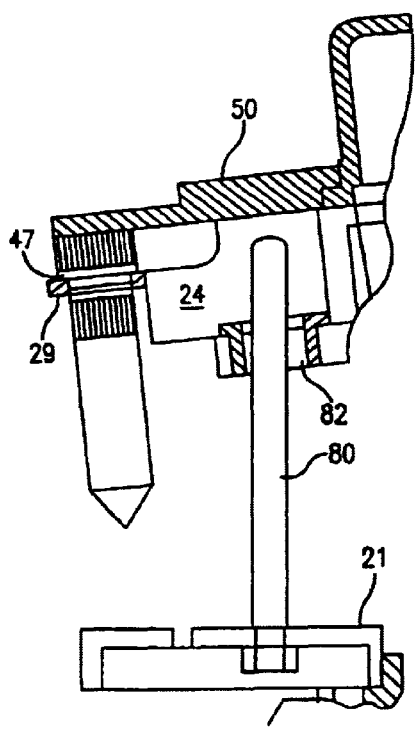
FIG. 9 is a fragmentary elevational view of the structure depicted in FIG. 8.

FIGS. 8 and 9 show a still further form of haltering means comprised of an upstanding post 80 carried on the anchor structure, and a passage 82 formed through the disc 24. The post 80 extends through the disc passage so that rotative movement of the disc is effectively barred.

Where the haltering means is susceptible to failure, an occurrence more likely where a resilient spring is used, it is important to provide a backup haltering means such as that 110 depicted in FIG. 1, such backup means being, e.g., the same as that depicted as a haltering means in FIG. 9.

Figure 10:
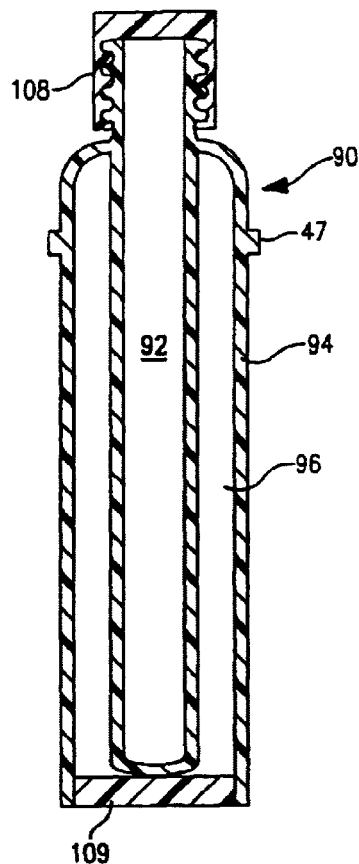
FIG. 10 is a vertical central sectional view on enlarged scale of a specimen vessel specially suited for use with the apparatus of the invention and which embodies a casing encircling the specimen holding part of the vessel, the casing holding a heat absorbing medium for drawing heat from the specimen and vessel during oscillation of the apparatus.

FIG. 10 shows a vial 90 that includes an inner compartment 92 for holding specimen material, small sized beads, etc. A casing wall 94 surrounds the outside of the inner compartment defining structure leaving a space 96 that can be filled with a heat transfer liquid such as water. Caps 108, 109 are used to seal entry to the inner compartment 92 and space 96. Prior to use, the vial can be placed in a freezer so as to chill the liquid which if water freezes to ice. When used, heat generated during oscillation of the vial can be absorbed by the fluid or ice which acts as a heat sink drawing heat away from the vial structure and the contents.

In effecting nucleic acid separation, it generally is best effected by rapidly reciprocally oscillating the tissue source material in the presence of bead-containing liquid medium at such a rate that produces an average linear acceleration in the source material which is in a range of about 150 g to about 415 g and at an oscillation rate between about 50 Hz to about 133 Hz the period involved for effecting separation being one in a range of time between about 10 to 120 seconds. Many protocols can be practiced with effective result using an oscillatory rate of about 100 Hz such as to produce average linear acceleration of at least about 300 g for a period of between 10 to 60 seconds.

The apparatus is used in conjunction with novel containers for conducting the isolation processes of the invention. The containers comprise a cover and a lower member for containing the extractant and other components, also referred to herein as the "holder". The holder can take a variety of forms both as to shape, size and material of manufacture, depending upon the intended use, which variables are not considered to be necessarily limiting to the invention, and which will be apparent to one skilled in the art. For example, the cover may alternately be considered a cap, lid, top, etc, and may attach by friction, seal, threads, clamp, etc., and may be removable from the lower member.

Figure 11:
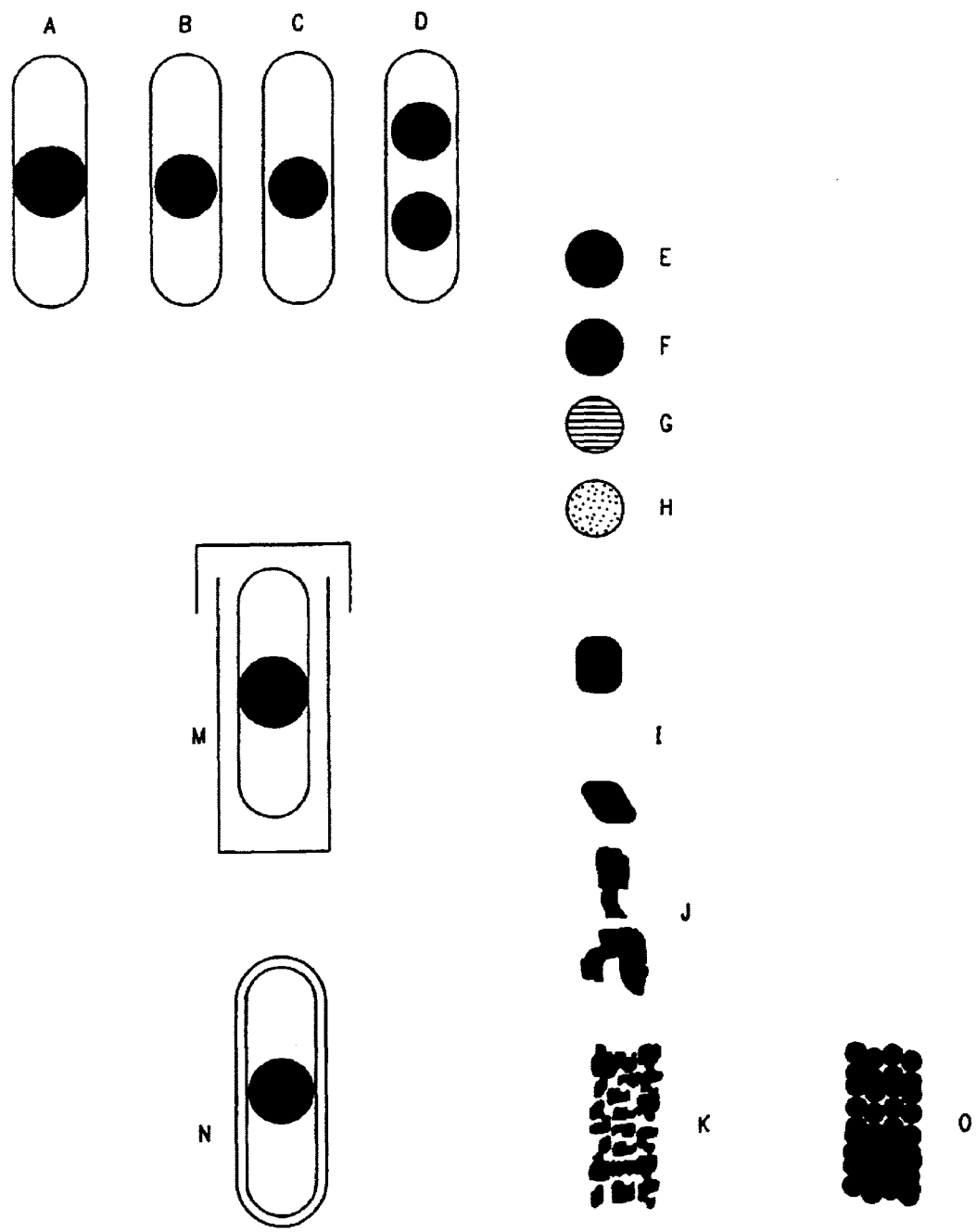
FIG. 11 illustrates in panels A–O various configurations of particles and containers for use in the present methods.

The container used in the present methods can also vary, but in some cases it may be desirable for the container to have concave ends so as to conform to the shape of the sphere, as illustrated in FIG. 11A or 11M. The advantages of conforming top and bottom ends are several, including increasing durability of the container during use by minimizing the stress to the ends during use, and increasing rupture effectiveness by removing dead "spaces" where larger tissue fragments can avoid impact by the bead.

In addition, the mechanism for securing the top to the container can vary, so long as the top is openable and yet can retain the contents during oscillation. Thus, the invention is not to be considered as limited to any particular container as container design is not a principle focus of the present invention. All the container embodiments, e.g., A–D and L–M, illustrate a bead in a container, which must necessarily be configured with an openable top, although the details of the top(s) are not defined.

A further permutation is illustrated in FIG. 11M, showing an inner and outer container, in which the inner container holding the sphere also has small pores of preselected diameter as in a cage to allow material out through the pores during the rupturing process to the extent of the pore diameter. This embodiment facilitates separation of the released suspension, including nucleic acids from insoluble or indestructible materials in the tissue. In this embodiment, the outer container collects the material which passed out through the pores, and "L" identifies a removable lid on the outer container.

In a particularly preferred embodiment, the container has substantially cylindrical walls such that when utilized with a spherical bead the effect is similar to a dounce homogenized, whereby the clearance between the inner walls of the container and the surface of the sphere can be adjusted so as to define the thickness of the article to be disrupted. In preferred embodiments, the clearance is selected to be less than the diameter of a cell in the tissue to be disrupted, such that by use the cells are broken without disrupting subcellular organelles. In other embodiments, the clearance is selected so as to disrupt both cell and nuclei without disrupting smaller subcellular organelles, such as microsomes and other vesicles that may contain nucleolytic enzymes. Thus, a clearance can be as small as the diameter of subcellular organelles, or on the order of 10, 25 and 50 microns (u), on up to the diameter of small cells, such as 100 u (0.1 mm), and on up to the diameter of large cells, such as about 3 mm.

A preferred clearance useful in the present methods is in the order of about 25 microns (0.025 mm) to about 3 millimeters (mm), preferably about 0.8 to 1.5 mm, and more preferably about 1 mm. Of course, the clearance achieved is a function of both the container inner diameter and the sphere utilized. Preferred are 1 to 2 ml containers and spheres having about 5 to 10 mm diameters.

In another embodiment, it is appreciated that the container can contain two or more spheres having different clearances for the purpose of specifically rupturing structures, tissues, cells and/or organelles in a coordinated manner. For example, whereas a very small clearance sphere may have difficulty initially with a crude sample, a large clearance sphere will rapidly break the sample into smaller diameter fragments which the smaller clearance sphere may then productively homogenize. Thus the invention contemplates the uses of combinations of clearances in two or more spheres.

For use in research and other laboratories where relatively small amounts of DNA are required, the containers can be packaged in kits containing one or a plurality of containers together with containers for buffers, reagents and other accoutrements appropriate to the practice of the present invention. The kits may further include a selection of containers with particles of different sizes and/or densities to accommodate the varying sizes of the cells or hardness of tissues employed as the DNA source material. Such containers are especially useful with an apparatus which can hold a plurality of containers, even up to 20 or more. Such machines and containers are especially useful when it is desired to conduct a number of DNA isolations simultaneously or sequentially.

2. Methods for Isolation of Nucleic Acid from Tissue

The present invention describes a method for disruption of tissues to facilitate release and ultimately recovery of selected cellular components, particularly nucleic acids, and more particularly DNA, in a purification procedure for those components.

The invention involves subjecting the tissue in a liquid medium to mechanical energy of a particular type as specified herein so as to disrupt tissue and cell structure sufficiently to release nucleic acids, and particularly DNA, into the liquid phase for subsequent recovery and purification.

As described herein, the choice of mechanical energy and disruption conditions depends upon the type of tissue to be disrupted, and the process may involve the use of one or more particles to assist the application of mechanical energy.

In addition, the release by mechanical energy is conducted by combining a tissue containing the DNA with a liquid medium in a closed container suitable for applying the mechanical energy.

The nucleic acid source material can be any source believed to contain nucleic acids, including bacteria, fungi or yeast cells, viruses, plant or animal tissue, foodstuffs, gels, process by-products, soil or water samples, industrial solutions, and the like materials having nucleic acids. The nucleic acid source material, cell or tissue can range in structural complexity, subcellular organelle content, and level of tissue organization, which differences contribute to the structural integrity, i.e., "hardness" or "softness" of the material from a mechanical disruption perspective, as described further herein.

The nucleic acid source material is typically provided as a paste or pellet if provided as a bacteria, fungi, yeast or any cultured cells, and as pieces of tissue in small fragments if derived from plants or animals. For example, single-cell suspensions of bacterial or yeast are typically provided by centrifugation or filtration to yield a pellet or a paste, which is conveniently transferred to a container as described herein suitable for applying the oscillatory mechanical energy.

In the case of plants or animals, the particular portion of the material, e.g., muscle, brain, kidney, etc., or leaf, seed, root, stem, etc., is collected, and may be fragmented to a convenient size of about 0.1 mm to 2 cm by a variety of methods including surgical sectioning, smashing to randomly break the tissue, fragmentation by freezing the tissue and then rapidly impacting the frozen tissue to shatter it into pieces, and the like fragmentation methods.

Freezing and shattering is particularly preferred because of the benefits of maintaining the provided biological tissue cold. Freezing is typically effected by immersion of the provided tissue into liquid nitrogen, or contacting the tissue with dry ice, until frozen. The shattering is typically effected by placing the frozen tissue into a plastic bag or foil container, and impacting the frozen tissue with a hammer with sufficient force to shatter the tissue into pieces.

The liquid medium is formulated to assist the disruption process, but may also contain materials to assist the recovery process. The liquid medium is typically a buffered cell resuspension solution. Exemplary liquid media are described further herein.

The total volume of the container used for applying the mechanical energy to the DNA source material should be sufficient so that when it is closed, it will hold the liquid medium, the DNA source material and the other components under conditions so that the entire mixture can be conveniently and efficiently shaken. A general rule for this purpose is that the total volume of the closed tube is about two-thirds (⅔) tissue/buffer and about ⅓ air space. If the container further contains particles to aid the mechanical lysis, the total volume of the closed tube is about ⅓ particles, ⅓ tissue/buffer, and about ⅓ air space.

In particular, the amount of particles can be an amount that occupies a volume approximately equal to about 1 to 100% of the liquid medium volume, although volumes of about 5 to 80%, and particularly about 10 to 50%, are more preferred.

DNA release from the cell or tissue structure of the source material is effected by the application of the specified mechanical energy for a predetermined time period. The time period of applied mechanical energy required depends principally upon the type of source material, the "hardness" of the tissue, and the size of the source from which the DNA is being extracted since these parameters for the various DNA sources such as bacteria, yeasts and plant or animal varies appreciably.

Time is not a particularly critical factor so long as a sufficient amount of time is used such that most of the DNA is released from the source, but not excessive time used so as to prevent excessive shearing of the DNA to be isolated. The particular time period used can be determined empirically by preparing samples of the material under one or more of the preferred conditions defined herein depending on the "hardness" of the source material. Exemplary times are described herein and in the Examples.

Following the release of the DNA into the liquid phase, any of a variety of DNA recovery methods may be used, including, but not limited to adsorption to a solid support, enzymatic treatment combined with selective precipitation, organic extraction, and the like methods described further herein.

Since rupture of the cell walls can release all of the cellular substituents, this invention can be used with or without chaotropic agents and extraction solvents such as those described herein to isolate other cellular components using known isolation procedures. For example, proteins may be isolated from a disrupted mixture containing an extraction solvent that comprises a neutral buffer and a cocktail of protease inhibitors.

As another example, the processes and containers of the invention may be used to efficiently and rapidly shred tissue such as skin, intestine, gastric, liver etc. into the component parts for the isolation of certain components. Individual cellular components, e.g., enzymes, may then be isolated using standard chromatographic techniques. Similarly, structural components e.g., connective tissue, membranes, cell wall components, etc. may be separated by differential centrifugation techniques.

3. Particles for Lysing Tissue

The invention deals with a method and apparatus specially suited for nucleic acid separation from its source material by subjecting that material to controlled mechanical energy as specified herein.

In one embodiment, the mechanical energy is applied in combination with particles of varying size, shape and density in the liquid medium containing the source material. It is believed that the presence of the particles increases the mechanical energy applied to the tissues, and provides a means for impacting, striking, breaking and/or rupturing the tissue so as to facilitate release of nucleic acids from the tissue and the DNA isolation process.

Any convenient number or weight of such particles may be employed, although the particular number and weight of particle somewhat depends upon the size and shape of the particle, and also on the particular tissue being treated, with the end objective of selecting a mechanical lysing force sufficient to release nucleic acid without compromising the quality of the recovered product.

The shape of particle may vary, including spherical, elliptical, rectangular, irregular, and the like shapes. Therefore, except for preferred embodiments, the terms "particle" and "bead" are used interchangeably to connote that various shapes may be utilized in the present invention. Exemplary shapes are shown in FIGS. 11A–11O.

The size of the particle also may vary depending on tissue type and scale of process, although particularly preferred are particles of from about 0.1 millimeter (mm) to about 2.0 centimeter (cm), and more preferably about 4 mm to 8 mm. In particular embodiments, it may be desirable to select the size of the bead relative to the container in which mechanical energy is directed, such that the clearance between the bead and the container internal wall defines the maximum diameter of tissue organelles that remain intact in the procedure, analogous to a Dounce homogenizer. Thus, FIGS. 11A–11C represent three different sized spheres (A–C) in which sphere A would homogenize to smaller sizes than sphere C, and sphere B would be intermediate, due to the respectively greater clearance in the container between sphere and container wall observed when using spheres A–C, respectively. It is seen that the bead size is dependent upon the scale of the procedure and the corresponding size of the container in which tissue sample, liquid medium and particle are to be oscillated.

Exemplary particle shapes besides spheres are illustrated in FIGS. 11I–11K, where 11I illustrates "odd" shapes with smooth edges and sides, 11J illustrates irregular shapes with non-smooth edges, and 11K illustrates the irregularly shaped particles of 11J in a smaller size and used as a cluster.

Beads used in the protocol can vary in density, which provides certain advantages. Beads that are relatively more dense provide the advantage of delivering relatively higher oscillation average linear acceleration forces to the specimen tissue which is advantageous where the "hardness" of the tissue to be ruptured is to be considered. Examples of the use of varying densities, e.g., plastic, glass, dense ceramic and steel, are described herein and demonstrate usefulness depending on the hardness of the tissue structure.

Preferred plastic beads are constructed of teflon, polypropylene or PVC. Preferred ceramic beads are zirconium silica oxide ceramic or silicon nitride ceramic. Metal beads should be corrosion resistant, and stainless steel is preferred.

Beads may also vary in porosity, as illustrated in FIGS. 11E–11H, where sphere E is solid, sphere F has fine pores, sphere G has medium pores, and sphere H has large pores.

B. Tissue Lysis Conditions for Varying Tissues

The most important feature of the preselected mechanical release conditions is that the conditions are capable of generating enough mechanical energy by reciprocal motion to break the tissue structure and cell walls and release the nucleic acids.

Whereas for soft tissues, efficient release may be accomplished solely by the mechanical forces upon the tissue in a liquid medium, other more structured tissues are ruptured by subjecting the tissue to rapidly oscillating particles or other inert particles in the liquid medium in the presence of the tissue. Such particles are commercially available in a variety of sizes from several sources as described further herein. The tissue, medium and particles are oscillated under preselected conditions depending on the tissue type to provide sufficient mechanical energy to disrupt the tissue and cell walls.

It is important to emphasize that for the isolation of DNA, the use of excessive mechanical energy is undesirable because it will shear the DNA to low molecular weight lengths that are not desirable.

1. Tissue Types

The process of the invention is applicable not only to biological tissue such as animal or plant tissues, but also to microorganisms such as bacteria, viruses, yeast, fungi, mold and the like materials as sources of DNA. Such sources, especially bacteria, yeast and plants are much more convenient than animal tissue as a source of DNA because they can be more uniform, are readily available in any desired quantities and can be easier to work with than animal tissue based on uniformity and quantity.

More important, however, is the consideration of the "type" of DNA source material used in the present methods. Because the structural integrity of the material, either at the level of subcellular organelles, cell walls or tissue structure, can vary depending on the type of material, the "hardness" of the material will also vary, affecting the choice of conditions under which the mechanical energy is applied to release high molecular weight DNA from the tissue/cell or non-cellular material.

For convenience, the "hardness" of a material or tissue can be broken down into four groups, termed "hard", "medium hard", "medium soft" and "soft" to connote a gradation between the most structurally intact materials/tissues that are relatively the most resistant to mechanical lysis, to the least structurally intact tissues that are relatively the least resistant to mechanical lysis.

A "soft" tissue is typically spleen, brain, liver, lymph, bone marrow, leukocytes, nucleated red blood cells, tissue cultured cells, soft foodstuff, gel, water sample, and the like soft tissues.

A "medium soft" tissue is typically kidney, heart, muscle, blood vessels, tumor or tissue biopsies, immature plant tissue such as fruit, flowers, sprouts, young leaves, nematodes such as *Caenorhabditis elegans*, gram negative bacteria such as *Escherichia coli*, gram positive bacteria such as *Staphylococcus aureus, Salmonella typhimurium*, or *Mycobacterium tuberculosis*, medium soft foodstuff, and like medium soft tissues.

A "medium hard" tissue is typically skin, cartilage, soft bone, tail snips (mouse tail), mature plant tissue such as mature leaves, tubers, legumes, chitinous tissues including whole insects such as mosquitos or fruit fly, slime mold such as *Dictyostelium discoideum*, yeast such as *Saccharomyces cerevisiae, Schizosaccharomyces pombe*, or *Pichia pastoris*, fungi such as Cryptococcus sp., algae, medium hard foodstuffs, and like medium hard tissues.

A "hard" tissue is typically plant seeds or bark, plant and tree trunks, stems, rice, soybean, oats, corn leaf, kernels, grain such as *Triticum aestivum* roots and other woody materials, bones, hard foodstuffs, soil or fossil samples, and like hard tissues.

The assignment of a tissue to a particular "hardness" is not to be construed as absolute as some tissues can vary in hardness depending on the condition of the source material. Therefore, in circumstances where mechanical release is not efficient, or alternatively is overly disruptive to the detriment of the released DNA, the "hardness" conditions should be varied empirically according to the various protocols described herein.

2. Lysis Conditions

DNA source material can be subjected to the mechanical energy according to the present invention under a variety of conditions designed to disrupt the tissue or cell structure and release the DNA into the liquid medium. The conditions will vary depending upon the hardness of the DNA source material to be treated, although certain aspects of the disruption process can be readily varied for efficient release as will be apparent to a skilled practitioner.

For example, the liquid medium may contain salts, buffers, stabilizers, detergents, and the like reagents.

Any of a wide variety of well known buffers which will permit control of the pH within the preferred ranges of about 5–9, preferably about 6.5–7.5, and more preferably about 7.0, may be employed. Buffers based on tris (hydroxymethyl)aminomethane (i.e., Tris), sodium acetate or sodium citrate are presently preferred because they are readily available and provide excellent results. Other buffers known to the skilled artisan may be used.

For research purposes, which normally require only small amounts of DNA, the amount of DNA source material, liquid medium and container may be very small. Typically, the total container volume is from about 1.0–3.0 ml. Larger containers may be employed to obtain greater quantities of DNA.

A preferred cell resuspension buffer for the disruption process contains buffer from about 5–500 millimolar (mM), and preferably is Tris-HCl. The buffer preferably contains EDTA in an amount of from 0.5–500 mM. A particularly preferred buffer is comprised of 50 mM Tris-HCl, pH 7.0, 20 mM EDTA.

A detergent may be included in the cell resuspension buffer. Typically, the detergent is included in the disruption procedures for more structured tissues, such as medium soft, medium hard and hard tissue to minimize DNA damage during the release procedure. It has been determined that detergent in the liquid medium during application of the mechanical energy prevents excessive shearing of DNA such that the isolated DNA is of high quality for subsequent use in recombinant DNA manipulations such as the polymerase chain reaction (PCR) and the like methods. Detergents are typically not employed to facilitate disruption of soft tissues, particularly where disruption is conducted in the absence of particles, as described further herein.

a. Disruption of Soft Tissue

Typical disruption conditions for soft tissues are relatively more gentle, and include the use of the above described preferred Tris-HCl/EDTA buffer in the liquid medium in a ratio of about 1:1 (v/v) material to liquid medium, and the application of about 25–75 hertz (Hz) oscillatory mechanical energy, more preferably about 50 Hz, to produce a gravitation of about 100–200 times gravity (×g), more preferably about 150×g, for a time period of about 5 to 60 seconds, preferably about 10 to 30 seconds, and more preferably about 20 seconds.

b. Disruption of Medium Soft Tissue

Typical disruption conditions for medium soft tissues are relatively more rigorous than for soft tissues, and include the use of the above described preferred Tris-HCl/EDTA buffer in the liquid medium in a ratio of about 1:1 (v/v) material to liquid medium, and the application of about 75–125 hertz (Hz) oscillatory mechanical energy, more preferably about 100 Hz, to produce a gravitation of about 200–400 times gravity (×g), more preferably about 300×g, for a time period of about 5 to 60 seconds, preferably about 20 to 40 seconds, and more preferably about 30 seconds.

For medium soft tissues, the application of mechanical energy is preferably conducted in the presence of one or more particles to assist the application of mechanical energy. Preferably, the particles used occupy a volume approximately equal to the volume of liquid medium such that the particle:liquid:material ratio is about 1:1:1 (v/v/v), although the ratio of particle to liquid can be from about 0.2:1 to about 2:1.

In preferred embodiments, the particle used is a sphericle bead as described herein, typically about 2–10 mm in diameter, although the precise diameter depends upon the container such that there is to be clearance of at least 0.5 mm, preferably about 1 mm, between the walls of the container and the sphere. In a preferred embodiment, the container has an inner diameter of 8 mm and the sphere is about 7 mm.

For disrupting medium soft tissue, it is also preferred that the particle be of relatively low mass so that the impacts delivered during application of the oscillatory mechanical energy are of relatively low momentum. Typical mass would be that provided by a non-brittle plastic sphere such as polypropylene and the like plastics.

Furthermore, for disruption of medium soft tissue to release high molecular DNA, it is preferred to include a detergent in the liquid medium at a concentration of about 0.1 to 10% weight per weight of liquid medium (w/w), preferably about 0.1 to 5%, more preferably about 0.5 to 3%, and more preferably about 1–2%. Typical detergents useful in the method are described herein, although particularly preferred is the use of 1 to 2% SDS in the liquid medium.

c. Disruption of Medium Hard Tissue

Typical disruption conditions for medium hard tissues are relatively more rigorous than for medium soft tissues, and include the use of the above described preferred Tris-HCl/EDTA buffer in the liquid medium in a ratio of about 1:1 (v/v) material to liquid medium, and the application of about 75–125 hertz (Hz) oscillatory mechanical energy, more preferably about 100 Hz, to produce a gravitation of about 200–400 times gravity (×g), more preferably about 300×g, for a time period of about 5 to 60 seconds, preferably about 20 to 40 seconds, and more preferably about 30 seconds.

For medium hard tissues, the application of mechanical energy is preferably conducted in the presence of one or more particles to assist the application of mechanical energy as was described above for medium soft tissues, with the following exceptions.

For disrupting medium hard tissue, it is preferred that the particle be of a medium mass so that the impacts delivered during application of the oscillatory mechanical energy are of relatively average momentum. Typical mass would be that provided by a non-brittle ceramic sphere such as Zirblast (Specialty Ball Co., Rochy Hill, Conn.) and the like ceramics.

Furthermore, for the disruption of medium hard tissue, it is preferred to include a detergent in the liquid medium as described above for medium soft tissues.

d. Disruption of Hard Tissue

Typical disruption conditions for hard tissues are relatively more rigorous than for medium hard tissues, and include the use of the above described preferred Tris-HCl/EDTA buffer in the liquid medium in a ratio of about 1:1 (v/v) material to liquid medium, and the application of about 75–125 hertz (Hz) oscillatory mechanical energy, more preferably about 100 Hz, to produce a gravitation of about 200–400 times gravity (×g), more preferably about 300×g, for a time period of about 5 to 120 seconds, preferably about 30 to 60 seconds, more preferably about 40 seconds.

For hard tissues, the application of mechanical energy is preferably conducted in the presence of one or more particles to assist the application of mechanical energy as was described above for medium soft and medium hard tissues, with the following exceptions.

For disrupting hard tissue, it is preferred that the particle be of a high mass so that the impacts delivered during application of the oscillatory mechanical energy are of relatively high momentum. Typical mass would be that provided by a metal sphere such as steel and the like relatively hard metals.

Furthermore, for the disruption of hard tissue, it is preferred to include a detergent in the liquid medium as described above for medium soft tissues.

3. Detergents

In preferred embodiments, particularly for the disruption of medium soft, medium hard and hard tissues, the liquid medium used for the application of oscillatory mechanical energy includes a detergent in the range of about 0.1 to 10% (w/v), preferably about 0.1% to 5%, more preferably about 0.5% to 3%, and still more preferably about 1 to 2%.

The selected detergent may be any of a variety of conventional surfactants including anionic, cationic, non-ionic and amphoteric surfactants.

Typically useful anionic detergents include, for example, sodium dodecyl sulfate (SDS), sodium-n-decyl sulfate and triethanolamine dodecyl benzene sulfonate.

Cationic detergents useful in the practice of the invention include, by way of example, cetyl trimethyl ammonium bromide and other N-alkyl quaternary ammonium halides, we well as polyethoxylated quaternary ammonium chloride.

Amongst the nonionic detergents, there are tallow fatty alcohol ethoxylates, ethoxylated tridecyl alcohol, ethoxylated tridecanol, nonyl phenol ethoxylate and octylphenoxy polyethoxy ethanol.

Amphoteric detergents include, for example cocoamidopropyl betaine, disodium tallowimino diprioionate and cocoamido betaine.

A particularly preferred surfactant is SDS.

All of these detergents, and many other equivalent surfactant compounds are readily available from commercial sources.

It is emphasized that the use of detergent is particularly preferred for the isolation of high molecular weight DNA from medium soft, medium hard and hard tissues. Based on the results shown in the Examples herein, it is seen that the shearing of DNA is excessive in the absence of detergent for isolation of DNA from the harder tissue, whereas lysis of soft tissue in the presence of detergent produces little or no lysis.

C. DNA Recovery Methods

Following release of the DNA into the liquid medium by the application of oscillatory mechanical energy, the released DNA can be recovered by any of a variety of well known DNA isolation methods. In this regard, the invention is not to be construed as limiting, although several preferred recovery methods are described.

Exemplary DNA recovery methods include (1) adsorption onto a solid matrix, such as silica, latex or polystyrene, followed by selective washing and elution of the washed DNA, (Sambrook et al., "Molecular Cloning: A Laboratory Manual" 2nd Ed., Cold Springs Harbor Press, 1989; and Reddy et al., "Current Protocols in Molecular Biology", 4.4.1–4.4.7, Ausebel, F. M., et al., Eds., Wiley, New York, 1991), (2) enzymatic treatment to digest protein and RNA, followed by salting out to remove protein and detergent (GNOME DNA ISOLATION KIT, Cat. No. 2010–200, BIO101, Inc., Vista, Calif.) and (3) extraction with organic solvents (Sambrook et al., supra, and Reddy et al., supra).

The following examples are given by way of illustration only and should not be considered limitations of this invention, many apparent variations of which are possible without departing from the spirit or scope thereof.

EXAMPLES

1. Reagents for Use in the Methods

The following reagents were prepared and used in practicing the methods of the invention.

A. Cell Resuspension Solution: 50 mM Tris-HCl, pH 7, 20 mM EDTA.
B. RNAse Solution: 50 mM Tris-HCl, pH 7, 5 mM EDTA, 5 mg/ml RNAse A.
C. Cell Lysis/Denaturing Solution: 1% SDS in Cell Resuspension Solution.
D. Protease Solution: 5 mg/ml Proteinase K, 5 mg/ml Pronase in Cell Resuspension Solution with 1% SDS.
E. Saltout Solution: 5 M NaCl.
F. Acetate Solution; 5 M potassium acetate.
G. Binding Matrix: 30% (V/V) silica matrix granules in 6 M guanidine thiocyanate.
H. Wash Solution: 10 mM Tris-HCl, pH 7, 1 mM EDTA, 100 mM NaCl, 50% ethanol.
I. 10% SDS in water.

2. Release of DNA from Intact Mouse Liver Tissue

Mouse liver was obtained fresh, and quick-frozen on dry ice. Thereafter, the frozen liver was smashed with a hammer into small tissue fragments, typically of about from 3 cubic millimeters ($mm^3$) to about 0.1 $mm^3$. Alternatively, fresh liver was sectioned to about 3–0.1 $mm^3$ fragments, and used directly.

One hundred milligrams (mg) of frozen liver tissue fragments or fresh, unfrozen tissue were weighed out directly into a 2.0 ml microcentrifuge tube (PGC Scientific, Gaithersburg, Md., Cat. #16-8115-34), 1.0 ml of Cell Resuspension Solution was added, and the resulting mixture was subjected to oscillatory mechanical energy in the oscillation apparatus described herein in the amount of 75 Hz producing about 200×g for 20 seconds to form a solution of disrupted cell components, including released DNA.

Liver tissue is considered a "soft" tissues and when treated in this manner can be readily disrupted by the above conditions to release their DNA for further isolation. DNA can also be prepared in this manner from brain, lymph, marrow, tissue cultured cells, non-tissue sources such as gels, soft foodstuffs, soil or water samples, and the like soft materials as described herein.

The resulting solution containing released DNA is then isolated in pure form from the other released cellular components by conventional DNA isolation methods. Exemplary are the two methods described herein using adsorption to silica particles described in Example 6, or using an enzymatic method as described in Example 7.

3. Release of DNA from Intact Mouse Kidney Tissue

Mouse kidney was obtained fresh, and quick-frozen on dry ice. Thereafter, the frozen kidney was smashed with a hammer into small tissue fragments, typically of about from 3 cubic millimeters ($mm^3$) to about 0.1 $mm^3$. Alternatively, fresh kidney was sectioned to about 3–0.1 $mm^3$ fragments, and used directly.

One hundred milligrams (mg) of frozen kidney tissue fragments or fresh, unfrozen tissue were weighed out directly into a 2.0 ml screw-capped microcentrifuge tube having substantially parallel walls of diameter 8 mm available from PGC Industries. A polypropylene sphere of 7 mm diameter available from Engineering Laboratories, Inc., N.Y., N.Y., and 1.0 ml of Cell Resuspension Solution containing 1% (w/v) sodium dodecyl sulfate (SDS) were added to the tissue fragments, and the resulting mixture was subjected to oscillatory mechanical energy in the oscillation apparatus described herein in the amount of about 100 Hz producing about 300×g for 30 seconds to form a solution of disrupted cell components, including released DNA.

Kidney tissue is considered a "medium soft" tissue and when treated in this manner can be readily disrupted by the above conditions to release their DNA for further isolation. DNA can also be prepared in this manner from heart, muscle, immature plant tissue such as fruit, sprouts, young leaves, gram negative or gram positive bacteria, and like medium soft materials as described herein.

The resulting solution containing released DNA is then isolated in pure form from the other released cellular components by conventional DNA isolation methods. Exemplary are the two methods described herein using adsorption to silica particles described in Example 6, or using an enzymatic method as described in Example 7.

4. Release of DNA from Intact Mouse Skin Tissue

Mouse skin was obtained fresh, and quick-frozen on dry ice. Thereafter, the frozen skin was smashed with a hammer into small tissue fragments, typically of about from 3 cubic millimeters ($mm^3$) to about 0.1 $mm^3$.

One hundred milligrams (mg) of frozen skin tissue fragments or fresh, unfrozen tissue were weighed out directly into a 2.0 ml screw-capped microcentrifuge tube having substantially parallel walls of diameter 8 mm available from PGC Industries. A ceramic sphere of 7 mm diameter available from Specialty Ball Co., Rocky Hill, Conn., and 1.0 ml of Cell Resuspension Solution containing 1% (w/v) sodium dodecyl sulfate (SDS) were added to the tissue fragments, and the resulting mixture was subjected to oscillatory mechanical energy in the oscillation apparatus described herein in the amount of about 100 Hz producing about 300×g for 30 seconds to form a solution of disrupted cell components, including released DNA.

Skin tissue is considered a "medium hard" tissue and when treated in this manner can be readily disrupted by the above conditions to release their DNA for further isolation. DNA can also be prepared in this manner from cartilage, soft bone, yeast cells, mature plant tissue such as mature leaves, tubers, legumes, chitinous tissues including whole insects, and like medium hard materials as described herein.

The resulting solution containing released DNA is then isolated in pure form from the other released cellular components by conventional DNA isolation methods. Exemplary are the two methods described herein using adsorption to silica particles described in Example 6, or using an enzymatic method as described in Example 7.

5. Release of DNA from Intact Plant Seeds

Seeds were obtained fresh from wheat and quick-frozen on dry ice. Thereafter, the frozen seeds were smashed with a hammer into small tissue fragments, typically of about from 3 cubic millimeters ($mm^3$) to about 0.1 $mm^3$.

One hundred milligrams (mg) of fragmented seeds were weighed out directly into a 2.0 ml screw-capped microcentrifuge tube having substantially parallel walls of diameter 8 mm available from PGC Industries. A steel sphere of 6 mm diameter available from Abbott Ball Co., Elmwood, Conn., and 1.0 ml of Cell Resuspension Solution containing 1% (w/v) sodium dodecyl sulfate (SDS) were added to the tissue fragments, and the resulting mixture was subjected to oscillatory mechanical energy in the oscillation apparatus described herein in the amount of about 100 Hz producing about 300×g for 40 seconds to form a solution of disrupted cell components, including released DNA.

Plant seeds are considered a "hard" tissue and when treated in this manner can be readily disrupted by the above conditions to release their DNA for further isolation. DNA can also be prepared in this manner from plant bark, plant and tree trunks, roots and other woody materials, bones, rice, and like hard materials as described herein.

The resulting solution containing released DNA is then isolated in pure form from the other released cellular components by conventional DNA isolation methods. Exemplary are the two methods described herein using adsorption to silica particles described in Example 6, or using an enzymatic method as described in Example 7.

6. Recovery of DNA Using Silica Adsorption

The silica binding matrix was silica obtained from BIO101, Inc. (Vista, Calif.) in the form of "Glassmilk®". The matrix comprises crushed silica particles having a range of sedimentation rate through still water at unit gravity of from 0.001 to 0.01 centimeters per minute (cm/min), an average size of from 0.5 to 8 microns, and a total size range of about 0.2 to 20 microns. The binding matrix was provided as a 30% (v/v) suspension in 6 M guanidine thiocyanate.

For DNA suspensions that do not contain SDS, such as the suspension prepared in Example 2, above, SDS was added from stock solution to produce a suspension with 1% SDS. The DNA suspensions containing SDS prepared as in Examples 3–5, above, were processed as follows without further treatment.

About 600 microliters of the DNA suspensions containing SDS were subjected to microcentrifugation at 15,000 rpm for 2 minutes to settle insoluble and precipitated materials. Thereafter, 350 ul of 5 M potassium acetate solution was added to precipitate SDS and protein, the suspension was mixed with the acetate by inverting the tube, and the mixture was microcentrifuged as before for 5 minutes to produce a detergent-free supernatant.

500 ul of the resulting detergent-free supernatant, by either methods, was then transferred to a 800 ul spin filter centrifuge tube (Spin Module™ centrifuge tube, BIO101, Inc., Vista, Calif.) and 300 ul of silica binding matrix was added. Thereafter, the spin tube was microcentrifuged as before for 2 minutes, and the flow-through in the decant trap of the spin tube was emptied. 700 ul of Wash Solution was added to the spin tube, and the tube was microcentrifuged as before for 2 minutes. The flow-through in the decant trap was emptied, and the spin tube was again microcentrifuged for 2 minutes to remove all excess liquid from the binding matrix. The spin filter was then transferred to a clean trap tube, 100 ul of water was added to the filter, the binding matrix was suspended in the water by flicking the tube, and the spin tube was then microcentrifuged as before for 2 minutes. The flow-through contained the eluted, isolated DNA in pure water.

7. Recovery of DNA Using Enzymatic Methods

DNA released into solution by the above described mechanical methods can also be recovered in pure form (isolated) by using selective enzymatic degradation of RNA and protein followed by salting-out the DNA.

To that end, to 1.0 ml of oscillated cell suspension from Examples 2–5 is added 50 ul of RNAse Solution, and the mixture is thoroughly mixed. Thereafter, 150 ul of 10% (w/v) SDS is added and thoroughly mixed if there was no SDS previously added, and the mixture is incubated at 55–65 degrees Centigrade (C) for 10 minutes. Thereafter, 35 ul of Protease Solution is added and thoroughly mixed, and incubated at 55 C. for 10 minutes, inverting occasionally. Thereafter, 450 ul of 5 M NaCl is added and thoroughly mixed to precipitate the SDS and proteins, and the mixture is microcentrifuged as before for 10 minutes at 4 C. The resulting clear supernatant is then removed with a large bore pipette tip and mixed with 1 ml water in a 15 ml tube, 4 ml of 100% ethanol is added, and the tube is slowly inverted end to end to precipitate the DNA. The resulting DNA is then spooled out of solution, dried, and redissolved as needed to yield isolated, pure DNA.

8. Effect of Detergent and Particles on DNA Isolation Method Using Soft Tissue

The DNA isolation method was carried out essentially as described in Example 2, except detergent and particles were varied to demonstrate the optimal mechanical energy conditions.

To that end, 100 mg of frozen rat liver was placed in each of four 2 ml microcentrifuge tubes as described earlier, and designated tubes A–D. A 5 mm diameter×3 mm width polypropylene disc was added to tubes B and D. One ml of Cell Resuspension Solution was added to each tube, and 100 ul of 10% SDS was added to tubes C and D, to produce 1% SDS final concentration. The clearance between the polypropylene disc and the centrifuge tube inner wall was about 3 mm when measured at the widest angle for the disc in the microcentrifuge tube. The four tubes were subjected to the same oscillatory mechanical energy in the apparatus as described herein delivering 75 Hz and about 200×g for 20 seconds to form a solution of disrupted liver tissue, with the degree of disruption varying among the tubes.

Figure 12:
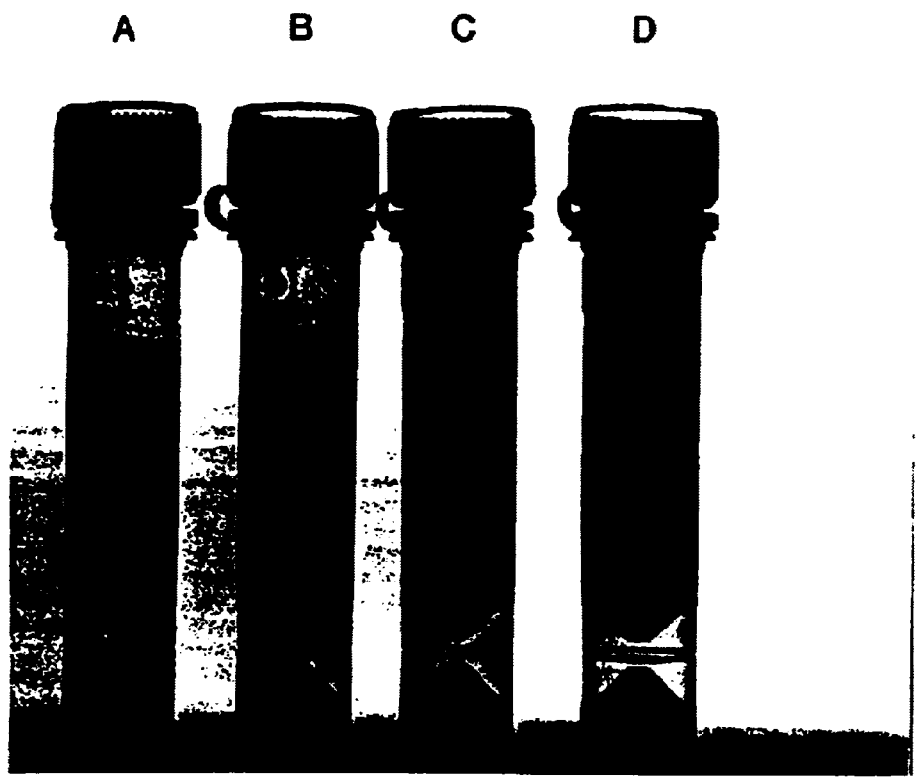
FIG. 12 presents a photograph of sample containers A–D, illustrating the appearance of containers of disrupted tissue according to the methods described in Example 8.

FIG. 12 shows a picture of the four tubes containing the disrupted liver solutions (A–D), illuminated by back lighting to illustrate the turbidity. Tubes A and B showed considerably more turbidity, and therefore more tissue and cell disruption than tubes C and D, indicating that the detergent almost completely inhibited tissue disruption, even in the presence of a particle. Without detergent (tubes A and B), the degree of lysis appears to be dramatically more extensive than with detergent (tubes C and D). Furthermore, the turbidity is more extensive when no particle disc was used (tube A) than when a polypropylene disc was used (tube B).

Figure 13:
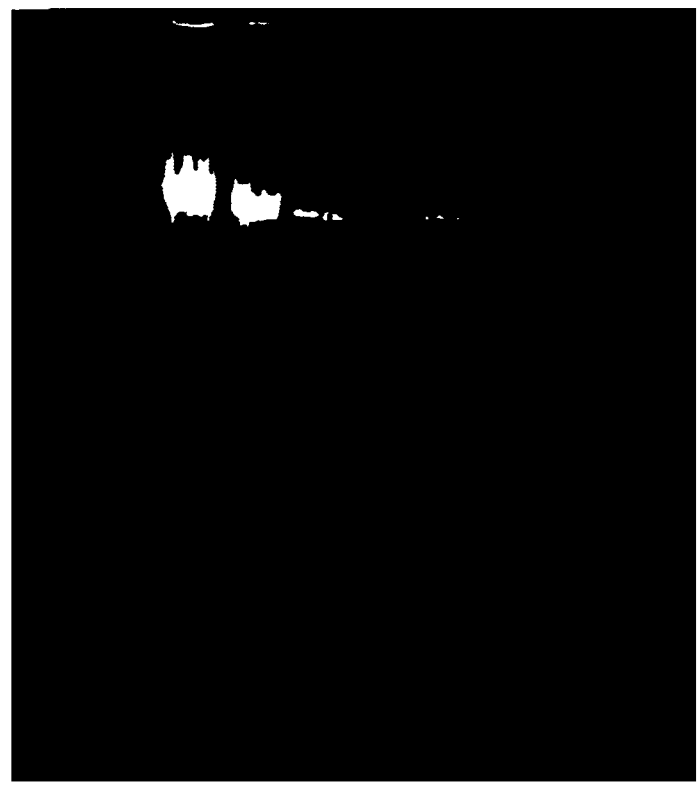
FIG. 13 illustrates the results of agarose gel electrophoresis, where lanes A–D correspond to samples A–D processed as described in Example 8.

Following mechanical energy disruption, the samples were subjected to centrifugation and DNA isolation according to the enzymatic method described in Example 7. The isolated DNA was then analyzed for yields and quality by agarose gel electrophoresis. Equal aliquots of DNA-containing samples produced from tubes A–D were electrophoresed and then stained with ethidium bromide. The results of the electrophoresed DNA are shown in FIG. 13. Both yield and quality of the DNA samples isolated in the absence of detergent are dramatically superior in terms of both amounts and higher molecular weight (samples A and B) when compared to DNA isolated in the presence of detergent (samples C and D). Furthermore, the yield and molecular weight of the isolated DNA is superior for DNA isolated in the absence of both detergent and a particle (sample A) compared to isolation without detergent but including a particle (sample B). In particular, the yield of DNA for samples C and D is estimated to be less than about 10% (by weight) of the amount isolated for sample A.

The results indicate that DNA isolated by the controlled mechanical energy method from soft tissue produces the highest yield and high molecular weight quality when energy is applied in the absence of both detergent and particles.

9. Variations in Detergent for Isolation of DNA from Medium Soft Plant Tissue

The effect of varying detergent concentrations during mechanical energy disruption of plant tissue for DNA isolation was analyzed. To that end, 100 mg of freshly picked young grass leaf was admixed in each in seven of 2 ml microcentrifuge tubes with 1 ml Cell Resuspension Solution and one 7 mm ceramic bead. Sufficient 10% SDS stock solution was added to the tubes to produce a final SDS concentration of 0.1% (tube 3), 0.4% (tube 4), 1% (tube 5), 2% (tube 6), 10% (tube 7). Control tubes 1 and 2 did not contain SDS during disruption step, with tube 2 having SDS added after the disruption step. The clearance between the ceramic sphere and the centrifuge tube inner wall was about 1 mm. The resulting mixtures were subjected to oscillatory mechanical energy using the apparatus described herein applying 100 Hz and about 300×g for 20 seconds to form a solution of disrupted plant cell components. Thereafter, the tubes were microcentrifuged at 12,000×g in a desktop microcentrifuge for 2 minutes to pellet debris, and the DNA in the supernatant was isolated as described in Example 6 using adsorption to silica particles.

Figure 14:
FIG. 14 illustrates the results of agarose gel electrophoresis, where Lanes 1–7 contain a sample from tubes 1–7, respectively, and Lane C contains control lambda DNA digested with Hind III as molecular weight markers, prepared as described in Example 9.

The resulting isolated DNA was then analyzed by agarose gel electrophoresis using equal aliquots from each sample, followed by ethidium bromide staining to visualize the electrophoresed DNA, and the electrophoresis results are shown in FIG. 14. The lanes of the gel contain samples as follows:

| Lane C | Lambda Hind III DNA marker |
|---|---|
| Lane 1 | tube 1 (+ bead, no SDS) |
| Lane 2 | tube 2 (+ bead, add 1% SDS after disruption) |
| Lane 3 | tube 3 (+ bead, 0.1% SDS) |
| Lane 4 | tube 4 (+ bead, 0.4% SDS) |
| Lane 5 | tube 5 (+ bead, 1% SDS) |
| Lane 6 | tube 6 (+ bead, 2% SDS) |
| Lane 7 | tube 7 (+ bead, 10% SDS) |

The results shown in FIG. 14 demonstrate that the amount of DNA shearing into lower molecular weight forms was inversely proportional to the amount of detergent present during the mechanical energy disruption step. The least amount of DNA shearing occurred in the presence of the highest amount of SDS tested (10%), and yields appear to be the highest with 2% SDS. Disruption of medium soft tissue using particles in the applied energy medium in the absence of detergent results in shearing of the high molecular weight DNA (lanes 2–3), whereas, addition of detergent increases both the efficiency of DNA isolation and the quality of isolated high molecular weight DNA.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A method of isolating high molecular weight nucleic acid from a biological material which comprises mechanically releasing the high molecular weight nucleic acid from the material by the application of rapidly oscillating reciprocal mechanical energy to the material in the presence of a liquid medium an a closed container to produce a released high molecular weight nucleic acid solution, wherein the released high molecular weight nucleic acid solution has an average molecular weight greater than 10 kilobases, the liquid medium contains one or more particles and detergent in an amount of from 0.1% to 10% weight per weight (w/w), wherein when the liquid medium contains more than one particle, the particles are identical or vary in size, shape, and density, and wherein the application of the energy is conducted by subjecting the container and thereby the material to oscillations at an oscillatory rate of between about 25 hertz (Hz) to about 166 Hz for a period of time of between about 3 seconds to about 5 minutes, the method further comprising recovering the high molecular weight nucleic acid from the liquid medium.

2. The method of claim 1, wherein the particles occupy a volume equal to about 5% to 80% of the liquid medium volume.

3. The method of claim 1, wherein the one or more particles is one spherical bead.

4. The method of claim 3, wherein the container has substantially cyclindrical walls and the spherical bead has a diameter of about 3 to 10 mm, and clearance between the spherical bead and the inner container wall is from about 0.025 to 3.0 mm.

5. The method of claim 3, wherein the spherical bead occupies a volume equal to from about 5% to 80% of the liquid medium volume.

6. The method of claim 1, wherein the biological material is a medium soft tissue, the oscillatory rate is about 100 Hz producing about 300×g, and the time period is about 20 to 45 seconds.

7. The method of claim 6, wherein the medium soft tissue is selected from the group consisting of heart, muscle, blood vessels, tumor or tissue biopsies, immature plant tissue, fruit, flowers, sprouts, young leaves, nematodes, culture cells, and bacteria.

8. The method of claim 1, wherein the biological material is a medium hard tissue, the oscillatory rate is about 100 Hz producing about 300×g, and the time period is about 20 to 45 seconds.

9. The method of claim 8, wherein the one or more particles is one spherical bead.

10. The method of claim 8, wherein the container has substantially cyclindrical walls, the spherical bead has a diameter of about 3 to 10 mm, and clearance between the spherical bead and the inner container wall is from about 0.025 to 3.0 mm.

11. The method of claim 10, wherein the clearance is about 1 mm.

12. The method of claim 8, wherein the medium hard tissue is selected from the group consisting of skin, cartilage, soft bone, tail snips, ear snips, mature plant tissue such as mature leaves, stems, tubers, legumes, chitinous tissues, whole insects, slime mold, yeast, algae, viruses, and fungi.

13. The method of claim 1, wherein the biological material is a hard tissue, the oscillatory rate is about 100 Hz producing about 300×g, the time period is about 30 to 60 seconds, and said container includes one or more steel spherical particles having a volume of about 1 to 50% of the liquid medium volume.

14. The method of claim 13, wherein the container has substantially cyclindrical walls, the spherical bead has a diameter of about 3 to 10 mm, and clearance between the spherical bead and the inner container wall is from about 0.025 to 3.0 mm.

15. The method of claim 13, wherein the hard tissue is selected from the group consisting of seeds, bark, plant stems, tree trunks, rice soybean, oats, wheat, corn leaf, kernels, grains, roots, bones, soil, and fossils.

16. The method of claim 1, wherein the recovering comprises treating the sample with an organic extraction procedure, a chaotropic salt procedure, or an enzymatic procedure prior to isolating the high molecular weight nucleic acid.

17. The method of claim 16, wherein the high molecular weight nucleic acid is isolated by lyophilization, freeze-drying, salt precipitation, or chromatographic methods.

18. The method of claim 1, wherein the recovering comprises removing non-high molecular weight nucleic acid components from the liquid medium by binding the components to a solid support.

19. The method of claim 1, wherein the recovering comprises removing non-high molecular weight nucleic acid components from the liquid medium by selectively precipitating or chromatographically removing the components.

20. The method of claim 1, wherein the recovering comprises removing high molecular weight nucleic acid components from the liquid medium by selectively precipitating the high molecular weight nucleic acid from non-high molecular weight components.

* * * * *